United States Patent [19]

Hutchinson et al.

[11] Patent Number: 5,563,064

[45] Date of Patent: Oct. 8, 1996

[54] PROCESS FOR PREPARING DAUNORUBICIN

[75] Inventors: Charles R. Hutchinson, Madison, Wis.; Krishna M. Madduri, Dowlaiswaram, Ind.; Francesca Torti; Anna L. Colombo, both of Milan, Italy

[73] Assignee: Farmitalia Carlo Erba S.R.L., Milan, Italy

[21] Appl. No.: 259,924

[22] Filed: Jun. 15, 1994

Related U.S. Application Data

[60] Division of Ser. No. 959,941, Oct. 9, 1992, Pat. No. 5,364,781, which is a continuation-in-part of Ser. No. 793,873, Nov. 18, 1991, abandoned.

[51] Int. Cl.⁶ .............. C12N 1/21; C12N 9/10; C12N 15/70

[52] U.S. Cl. ............... 435/252.3; 435/252.33; 435/252.35; 435/172.3; 435/320.1; 435/193; 435/69.1; 536/23.2; 536/23.7; 536/23.1

[58] Field of Search .................. 435/69.1, 193, 435/78, 886, 888, 172.3, 320.1, 252.3, 252.33, 252.35; 530/412, 350; 930/240; 536/23.2; 935/14

[56] References Cited

U.S. PATENT DOCUMENTS 5,364,781  11/1994  Hutchinson et al. ............ 435/193

OTHER PUBLICATIONS

Madduri et al. 1993 J. Bacteriol. 175, 3900–3904.
Otten et al. 1990. J. Bacteriol. 172, 3427–3434.
Conners et al. 1990. J. Gen. Microbiol. 136, 1895–1898.
Martin et al. 1984. Bio/Technol. 2, 63–71.
Vara et al. 1989 J. Bacteriol. 171, 5872–5881.
Yanisch–Perron et al. 1985 Gene 33, 103–109.
Tabor et al. 1985 Proc. Natl. Acad Sci. USA 82, 1074–1078.
Watson et al., 1987, in: *Molecular Biology Of The Gene*, Fourth Edition, Benjamin/Cummings Publishing Co., Menlo Park, CA, p. 313.
Connors et al., 1990, "Biosynthesis of anthracyclines: carminomycin 4–O–methyltransferase, the terminal enzymic step in the formation of daunomycin" J. Gen. Microbiol., 136, 1895–1898.
Bradshaw et al. (eds.), 1990, in: *Proteins: Form and Function*, Elsevier Trends J. Cambridge. (Elsevier Sci. Publ.) pp. 1–19.
Connors et al., 1993, "Partial purification and properties of carminomycin 4–O–thyltransferace from *Steptomyces* sp. strain C5 J. Gen Microbiol"., 139, 1353–1362.

*Primary Examiner*—Christopher S. F. Low
*Attorney, Agent, or Firm*—Nikaido, Marmelstein, Murray and Oram LLP

[57] ABSTRACT

The ability to convert carminomycin to daunorubicin can be conferred on a host by transforming the host with a recombinant vector comprising a DNA having the configuration of restriction sites shown in FIGS. 2, 3 and 4 and a nucleotide sequence shown in FIG. 3 of the accompanying drawings or a restriction fragment derived therefrom containing a gene coding for carminomycin 4-O-methyltransferase.

8 Claims, 6 Drawing Sheets

Fig. 3a

```
(SEQ ID NO: 1)
    S
    p
    h
    I
    GCATGCCGGCAACCGGGCGCCGGTTCTCCGGTGAGCAGATCCACCTCATCCGCATCGTC
  2 ---+---------+---------+---------+---------+---------+----- 60
    CGTACGGCCGTTGGCCCGCGGCCAAGAGGCCACTCGTCTAGGTGGAGTAGGCGTAGCAG

GACGGCAAGATCCGCGATCACCGCGACTGGCCCGACTACCTCGGCACCTACCGCCAGCTC
 61 ----+---------+---------+---------+---------+---------+----- 120
    CTGCCGTTCTAGGCGCTAGTGGCGCTGACCGGGCTGATGGAGCCGTGGATGGCGGTCGAG

GGCGAGCCCTGGCCCACCCCCGAGGGCTGGCGCCCCTGACCCCCCATCACCCCGCCGACG
121 ----+---------+---------+---------+---------+---------+----- 180
    CCGCTCGGGACCGGGTGGGGGCTCCCGACCGCGGGGACTGGGGGGTAGTGGGGCGGCTGC

CCACGACAGGAGCACGGACACACCATGACAGCCGAACCGACGGTCGCGGCCCGGCCGCAG
181 ----+---------+---------+---------+---------+---------+----- 240
    GGTGCTGTCCTCGTGCCTGTGTGGTACTGTCGGCTTGGCTGCCAGCGCCGGGCCGGCGTC

N
                                          c
                                          o
                                          I
    CAGATCGACGCCCTCAGGACCCTGATCCGCCTCGGAAGCCTGCACACGCCCATGGTCGTC
241 ----+---------+---------+---------+---------+---------+----- 300
    GTCTAGCTGCGGGAGTCCTGGGACTAGGCGGAGCCTTCGGACGTGTGCGGGTACCAGCAG

CGGACGGCCGCCACCCTGCGGCTCGTCGACCACATCCTGGCCGGGGCCCGCACCGTGAAG
301 ----+---------+---------+---------+---------+---------+----- 360
    GCCTGCCGGCGGTGGGACGCCGAGCAGCTGGTGTAGGACCGGCCCCGGGCGTGGCACTTC

GCCCTGGCGGCCAGGACAGACACCCGGCCGGAAGCACTCCTGCGACTGATCCGCCACCTG
361 ----+---------+---------+---------+---------+---------+----- 420
    CGGGACCGCCGGTCCTGTCTGTGGGCCGGCCTTCGTGAGGACGCTGACTAGGCGGTGGAC

X
                   h
                   o
                   I
    GTGGCGATCGGACTGCTCGAGGAGGACGCACCGGGCGAGTTCGTCCCGACCGAGGTCGGC
421 ----+---------+---------+---------+---------+---------+----- 480
    CACCGCTAGCCTGACGAGCTCCTCCTGCGTGGCCCGCTCAAGCAGGGCTGGCTCCAGCCG

GAGCTGCTCGCCGACGACCACCCAGCCGCGCAGCGTGCCTGGCACGACCTGACGCAGGCC
481 ----+---------+---------+---------+---------+---------+----- 540
    CTCGACGAGCGGCTGCTGGTGGGTCGGCGCGTCGCACGGACCGTGCTGGACTGCGTCCGG

GTGGCGCGCGCCGACATCTCCTTCACCCGCCTCCCCGACGCCATCCGTACCGGCCGCCCC
541 ----+---------+---------+---------+---------+---------+----- 600
    CACCGCGCGCGGCTGTAGAGGAAGTGGGCGGAGGGGCTGCGGTAGGCATGGCCGGCGGGG

ACGTACGAGTCCATCTACGGCAAGCCGTTCTACGAGGACCTGGCCGGCCGCCCCGACCTG
601 ----+---------+---------+---------+---------+---------+----- 660
    TGCATGCTCAGGTAGATGCCGTTCGGCAAGATGCTCCTGGACCGGCCGGCGGGGCTGGAC
```

Fig. 3b

```
         CGCGCGTCCTTCGACTCGCTGCTCGCCTGCGACCAGGACGTCGCCTTCGACGCTCCGGCC
661      ----+---------+---------+---------+---------+---------+-----  720
         GCGCGCAGGAAGCTGAGCGACGAGCGGACGCTGGTCCTGCAGCGGAAGCTGCGAGGCCGG

GCCGCGTACGACTGGACGAACGTCCGGCATGTGCTCGACGTGGGTGGCGGCAAGGGTGGT
721      ----+---------+---------+---------+---------+---------+-----  780
         CGGCGCATGCTGACCTGCTTGCAGGCCGTACACGAGCTGCACCCACCGCCGTTCCCACCA

TTCGCCGCGGCCATCGCGCGCCGGGCCCCGCACGTGTCGGCCACCGTGCTGGAGATGGCG
781      ----+---------+---------+---------+---------+---------+-----  840
         AAGCGGCGCCGGTAGCGCGCGGCCCGGGGCGTGCACAGCCGGTGGCACGACCTCTACCGC

GGCACCGTGGACACCGCCCGCTCCTACCTGAAGGACGAGGGCCTCTCCGACCGTGTCGAC
841      ----+---------+---------+---------+---------+---------+-----  900
         CCGTGGCACCTGTGGCGGGCGAGGATGGACTTCCTGCTCCCGGAGAGGCTGGCACAGCTG

GTCGTCGAGGGGGACTTCTTCGAGCCGCTGCCCCGCAAGGCGGACGCGATCATCCTCTCT
901      ----+---------+---------+---------+---------+---------+-----  960
         CAGCAGCTCCCCCTGAAGAAGCTCGGCGACGGGGCGTTCCGCCTGCGCTAGTAGGAGAGA
                                                     B
                                                     a
                                                     m
                                                     H
                                                     I
         TTCGTCCTCCTCAACTGGCCGGACCACGACGCCGTCCGGATCCTCACCCGCTGCGCCGAG
961      ----+---------+---------+---------+---------+---------+----- 1020
         AAGCAGGAGGAGTTGACCGGCCTGGTGCTGCGGCAGGCCTAGGAGTGGGCGACGCGGCTC

GCCCTGGAGCCCGGCGGGCGCATCCTGATCCACGAGCGCGACGACCTCCACGAGAACTCG
1021     ----+---------+---------+---------+---------+---------+----- 1080
         CGGGACCTCGGGCCGCCCGCGTAGGACTAGGTGCTCGCGCTGCTGGAGGTGCTCTTGAGC
                                 S
                                 s
                                 t
                                 I
         TTCAACGAACAGTTCACAGAGCTCGATCTGCGGATGCTGGTCTTCCTCGGCGGTGCCCTG
1081     ----+---------+---------+---------+---------+---------+----- 1140
         AAGTTGCTTGTCAAGTGTCTCGAGCTAGACGCCTACGACCAGAAGGAGCCGCCACGGGAC

CGCACCCGCGAGAAGTGGGACGGCCTGGCCGCGTCGGCGGGCCTCGTGGTCGAGGAGGTG
1141     ----+---------+---------+---------+---------+---------+----- 1200
         GCGTGGGCGCTCTTCACCCTGCCGGACCGGCGCAGCCGCCCGGAGCACCAGCTCCTCCAC

CGGCAACTGCCGTCGCCGACCATCCCGTACGACCTCTCGCTCCTCGTCCTTGCCCCCGCG
1200     ----+---------+---------+---------+---------+---------+----- 1260
         GCCGTTGACGGCAGCGGCTGGTAGGGCATGCTGGAGAGCGAGGAGCAGGAACGGGGGCGC

GCCACCGGCGCCTGACACACGAGGTACGGGAAGGGTTCATCAGCAATGCCGACACGCATG
1261     ----+---------+---------+---------+---------+---------+----- 1320
         CGGTGGCCGCGGACTGTGTGCTCCATGCCCTTCCCAAGTAGTCGTTACGGCTGTGCGTAC

ATCACCAACGATGAGGTGACCCTGTGGAGCGAAGGGCTCGGCGATCCGGCCGACGCCCCG
1321     ----+---------+---------+---------+---------+---------+----- 1380
         TAGTGGTTGCTACTCCACTGGGACACCTCGCTTCCCGAGCCGCTAGGCCGGCTGCGGGGC
```

Fig. 3c

```
          TTGCTCCTGATCGCCGGCGGCAACCTCTCGGCCAAATCGTGGCCGGACGAGTTCGTCGAA
1381 ----+---------+---------+---------+---------+---------+----- 1440
          AACGAGGACTAGCGGCCGCCGTTGGAGAGCCGGTTTAGCACCGGCCTGCTCAAGCAGCTT

CGCCTGGTCGCGGCCGGGCACTTCGTGATCCGCTACGACCACCGGGACACCGGGCGCTCC
1441 ----+---------+---------+---------+---------+---------+----- 1500
          GCGGACCAGCGCCGGCCCGTGAAGCACTAGGCGATGCTGGTGGCCCTGTGGCCCGCGAGG

TCCCGGTGCGACTTCGCGCTCCACCCCTACGGCTTCGACGAGCTGGCCGCCGACGCGCTG
1501 ----+---------+---------+---------+---------+---------+----- 1560
          AGGGCCACGCTGAAGCGCGAGGTGGGGATGCCGAAGCTGCTCGACCGGCGGCTGCGCGAC

GCCGTCCTGGACGGCTGGCAGGTCCGCGCCGCCCATGTGGTGGGCATGTCGCTGGGCAAC
1561 ----+---------+---------+---------+---------+---------+----- 1620
          CGGCAGGACCTGCCGACCGTCCAGGCGCGGCGGGTACACCACCCGTACAGCGACCCGTTG

P
              v
              u
              I
              I
     ACCATCGGCCAGC
1621 ----+-------- 1630
     TGGTAGCCGGTCG
```

Deduced amino acid sequence of carminomycin 4-O-methytransferase
(SEQ ID NO:2)

```
  1  MTAEPTVAAR  PQQIDALRTL  IRLGSLHTPM  VVRTAATLRL  VDHILAGART

51  VKALAARTDT  RPEALLRLIR  HLVAIGLLEE  DAPGEFVPTE  VGELLADDHP

101  AAQRAWHDLT  QAVARADISF  TRLPDAIRTG  RPTYESIYGK  PFYEDLAGRP

151  DLRASFDSLL  ACDQDVAFDA  PAAAYDWTNV  RHVLDVGGGK  GGFAAAIARR

201  APHVSATVLE  MAGTVDTARS  YLKDEGLSDR  VDVVEGDFFE  PLPRKADAII

251  LSFVLLNWPD  HDAVRILTRC  AEALEPGGRI  LIHERDDLHE  NSFNEQFTEL

301  DLRMLVFLGG  ALRTREKWDG  LAASAGLVVE  EVRQLPSPTI  PYDLSLLVLA

351  PAATGA*
```

PROCESS FOR PREPARING DAUNORUBICIN

This is a division of application Ser. No. 07/959,941, filed Oct. 9, 1992, now U.S. Pat. No. 5,364,781 which is a continuation-in-part of U.S. Ser. No. 07/793,873, filed on Nov. 18, 1991, abandoned.

FIELD OF THE INVENTION

The present invention concerns a way to produce anthracyclines useful in the treatment of cancer by modifying the biosynthesis of daunorubicin so as to improve the production of daunorubicin from carminomycin in streptomycetes other than *Streptomyces peucetius* 29050 and in bacterial cell extracts or by purified enzymes derived therefrom.

BACKGROUND OF THE INVENTION

The anthracyclines of the daunorubicin group, such as doxorubicin, carminomycin and aclacinomycin, are among the most widely employed agents in antitumoral therapy [F. Arcamone, *Doxorubicin*, Academic Press, New York, 1981, pp 12–25; A. Grein, *Process Biochem*, 16:34 (1981); T. Kaneko, Chimicaoggi May:11 (1988)]. Improved derivatives of daunorubicin and doxorubicin have been made by chemical synthesis to enhance their antitumor activity, particularly by the oral route of administration, and to combat the acute toxicity and chronic cardiotoxicity associated with the use of these drugs in the treatment of cancer [Penco, *Process Biochem*, 15:12 (1980); T. Kaneko, *Chimicaoggi* May:11 (1988)]. 4-Epidoxorubicin (Epirubicin®) and 4-demethoxydaunorubicin (Idarubicin®) are examples of such analogs.

These naturally occuring compounds are produced by various strains of Streptomyces (*S. peucetius, S. coeruleorubidus, S. galilaeus, S. griseus, S. griseoruber, S. insignis, S. viridochromogenes, S. bifurcus* and Streptomyces sp strain C5) and by *Actinomyces carminata*. Doxorubicin is only produced by *S. peucetius* subsp. caesius but daunorubicin is produced by *S. peucetius* as well as the other Streptomyces described above. The type strains *S. peucetius* subsp caesius IMRU 3920 (this strain is the same as ATCC 27952 and hereinafter is abbreviated to "*S. peucetius* 3920") *S. peucetius* ATCC 29050 ("*S. peucetius* 29050"), and *S. peucetius* subsp. caesius ATCC 27952 ("*S. peucetius* 27952") are publically available and are described in U.S. Pat. No. 3,590,028. *S. peucetius* 29050 and 27952 have been deposited at the American Type Culture Collection, Rockville, Md. USA, receiving the index number ATCC 29050 and 27952.

The anthracycline doxorubicin (2) is made by *S. peucetius* 27952 from malonic acid, propionic acid, and glucose by the pathway shown in FIG. 1 of the accompanying drawings ε-Rhodomycinone (4), carminomycin (3) and daunorubicin (1) are established intermediates in this process [Grein, *Advan. Appl. Microbiol.* 32:203 (1987), Eckardt and Wagner, *J. Basic Microbiol.* 28:137 (1988)]. Two steps in this pathway involve the O-methylation of discrete intermediates: the conversion of aklanonic acid to methyl aklanonate and carminomycin (3) to daunorubicin (1). Cell-free extracts of *S. peucetius* 29050, *S. insignis* ATCC 31913, *S. coeruleorubidus* ATCC 31276 and Streptomyces sp. C5 have been shown to catalyze the latter step in the presence of S-adenosyl-L-methionine [Connors et al., *J. Gen Microbiol*, 136:1895 (1990)], suggesting that all of these strains contain a specific carminomycin 4-O-methyltransferase (COMT protein).

Genes for daunorubicin biosynthesis and daunorubicin resistance have been obtained from *S. peucetius* 29050 and *S. peucetius* 27952 by cloning experiments [Stutzman-Engwall and Hutchinson, *Proc Natl. Acad. Sci*, USA 86:3135 (1988); Otten et al., *J. Bacteriol.* 172:3427 (1990)]. These studies have shown that, when introduced in *Streptomyces lividans* 1326, these cloned genes confer the ability to produce ε-rhodomycinone and to become resistant to daunorubicin and doxorubicin to this host. In subsequent work we examined whether these clones could confer the ability to convert carminomycin to daunorubicin when introduced into *S. lividans*. We have now isolated a 1.6 kilobase (kb) DNA segment that incorporates the carminomycin 4-O-methyltransferase gene, which hereinafter will be abbreviated as "dnrK".

SUMMARY OF THE INVENTION

The present invention provides DNAs having the configuration of restriction sites shown in FIG. 2 of the accompanying drawings or a restriction fragment derived therefrom containing a gene, dnrK, coding for carminomycin 4-O-methyltransferase. For convenience, the DNA segment shown in FIG. 2 is called here "insert DNA" and is further defined by the DNA sequence shown in FIG. 3 of the accompanying drawings. The invention also provides:

(1) recombinant vectors that are capable of transforming a host cell and that contain an insert DNA of a restriction fragment derived therefrom containing the dnrK gene;

(2) recombinant vectors that are able to increase the number of copies of the dnrK gene and the amount of its product in a strain of Streptomyces spp. producing daunorubicin;

(3) recombinant vectors that are able to express the dnrK gene in *Escherichia coli* so as to enable the production of the purified carmnomycin 4-O-methyltransferase enzyme;

4) a microbial source of carminomycin 4-O-methyltransferase for the bioconversion of carminomycin into pure daunorubicin.

BRIEF DESCRIPTION OF THE DRAWINGS

FIGS. 3a, 3b and 3c are a schematic illustration of a nucleotide sequence of the dnrK DNA segment which corresponds to that encoding carminomycin 4-O-methyltransferase. This covers the region between the SphI and the PvuII restriction sites of pWHM902 and shows the coding strand in the 5' to 3' direction. The derived amino acid sequence of the translated open reading frame encoding carminomycin 4-O-methyltransferase is shown below the nucleotide sequence of the dnrK gene. (SEQ ID NO:1, SEQ ID NO:2)

DETAILED DESCRIPTION OF THE INVENTION

Figure 1:
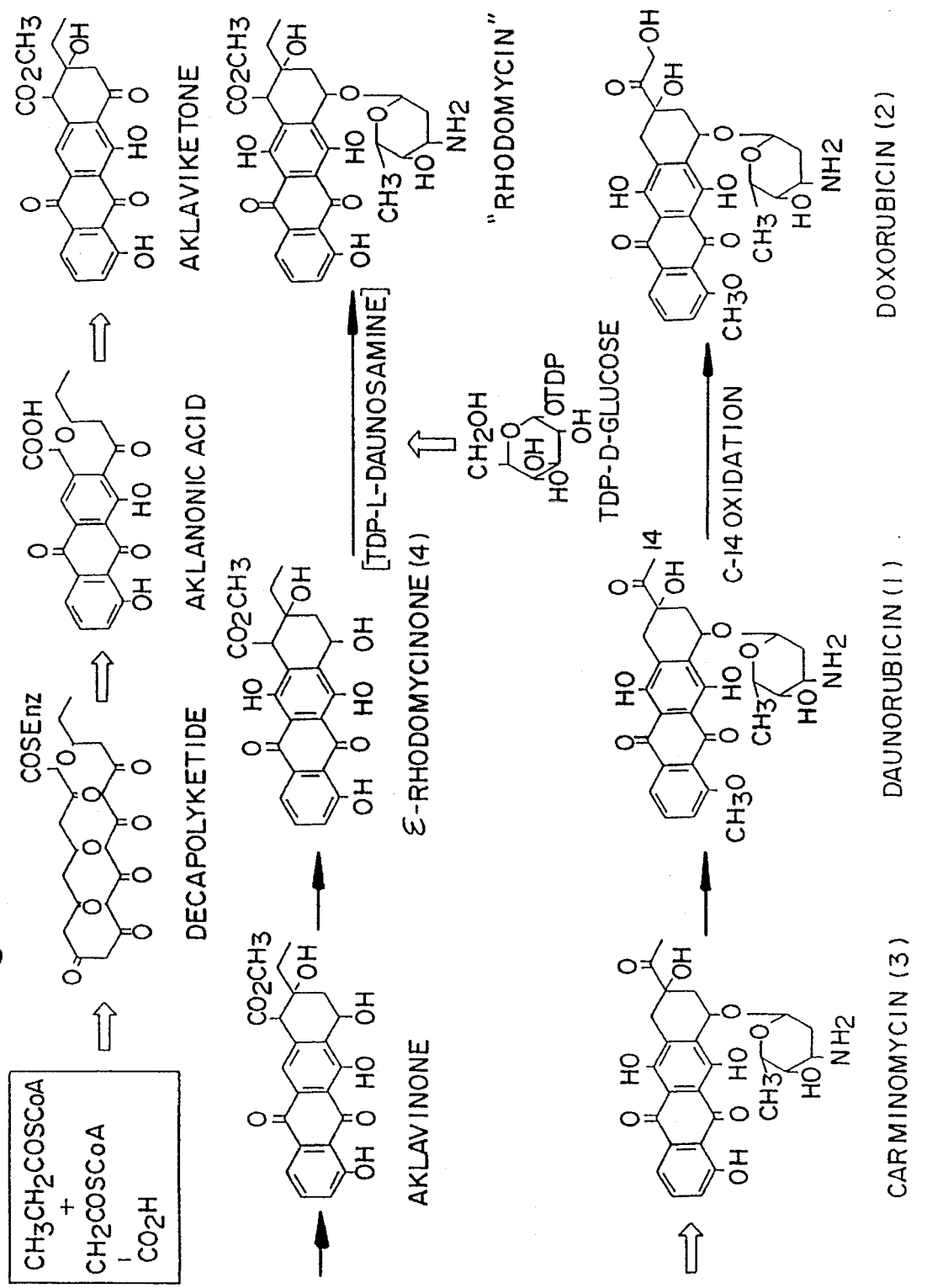
FIG. 1 is a summary of the doxorubicin biosynthetic pathway.

The insert DNAs and restriction fragments of the invention contain a gene (dnrK) coding for carminomycin 4-O-methyltransferase. For such a gene to be expressed, the DNA may carry its own transcriptional control sequence and, in particular, its own promoter which is operably connected to the gene and which is recognised by a host cell RNA polymerase. Alternatively, the insert DNA or restriction fragment may be ligated to another transcriptional control sequence in the correct fashion or cloned into a vector at a restriction site appropriately located neighboring a transcriptional control sequence in the vector.

An insert DNA or restriction fragment carrying a carminomycin 4-O-methyltransferase gene may be cloned into a recombinant; DNA cloning vector. Any autonomously replicating and/or integrating agent comprising a DNA molecule to which one or more additional DNA segments can be added may be used. Typically, however, the vector is a plasmid. A preferred plasmid is the high copy number plasmid pWHM3 or plJ702 [Katz et al., *J. Gen. Microbiol.* 129:2703 (1983)]. Other suitable plasmids are plJ385 [Mayeri et al., *J. Bacteriol.* 172:6061 (1990)], plJ680 (Hopwood et al., *Genetic manipulation of Streptomyces. A Laboratory Manual*, John Innes Foundation, Norwich, UK, 1985), pWHM601 [Guilfoile and Hutchinson, *Proc Natl. Acad. Sci. USA* 88:8553 (991)] or pPM927 [Smokina et al., *Gene* 94:52 (1990)]. Any suitable technique may be used to insert the insert DNA or restriction fragment thereof into the vector. Insertion can be achieved by ligating the DNA into a linearized vector at an appropriate restriction site. For this, direct combination of sticky or blunt ends, homopolymer tailing, or the use of a linker or adapter molecule may be employed.

The recombinant vector is used to transform a suitable host cell. The host cells may be ones that are carminomycin- or daunorubicin-sensitive, i.e., cannot grow in the presence of a certain amount of carminomycin or daunorubicin, or that are carminomycin- or daunorubicin-resistant. The host may be a microorganism. Strains of *S. peucetius*, in particular *S. peucetius* 29050, and other strains of Streptomyces species that produce anthracyclines or do not produce them may therefore be transformed. Transformants of Streptomyces strains are typically obtained by protoplast transformation. The dnrK gene may also be incorporated into other vectors and expressed in non-streptomycetes like *E. coli*. The COMT protein obtained by the transformed host may be employed for bioconverting carminomycin to daunorubicin. This method would allow the preparation of highly pure daunorubicin starting from a cell extract produced by a fermentation process and containing the undesired intermediate carminomycin besides the daunorubicin.

The bioconversion process can be carried out either by using directly the free or immobilized transformed cells or by isolating the COMT protein, which can be used in the free form, immobilized according to known techniques to resins, glass, cellulose or similar substances by ionic or covalent bonds, or grafted to fibers permeable to the substrate or insolubilized by cross-linkage. The COMT protein may also be used in the raw cellular extract.

The recombinant vector of the present invention may be also used to transform a suitable host cell, which produces daunorubicin, in order to enhance the bioconversion of carminomycin and to minimize the presence of said unwanted intermediate into the final cell extract. The host cells may be ones that are carminomycin, daunorubicin or doxorubicin-resistant, i.e., can grow in the presence of any amount of carminomycin, daunorubicin or doxorubicin. Strains of *S. peucetius*, in particular *S. peucetius* 29050, and other strains of Streptomyces species that produce anthracyclines may therefore be transformed. Transformants of Streptomyces strains are typically obtained by protoplast transformation. Daunorubicin can be obtained by culturing a transformed strain of *S. peucetius* or another Streptomyces species that does not contain a dnrK gene and recovering the daunorubicin or related anthracyclines thus-produced.

The insert DNAs are obtained from the genomic DA of *S. peucetius* 29050. This strain has been deposited at the American Type Culture Collection, Rockville, Md., USA under the accession number ATCC 29050. A strain derived from *S. peucetius* 29050, like *S. peucetius* 227952, may also be used, which typically will also be able to convert carminomycin to daunorubicin. Insert DNAs may therefore be obtained by:

(a) preparing a library of the genomic DNA of *S. peucetius* 29050 or a strain derived therefrom;

(b) screening the library for clones with the ability to convert carminomycin to daunorubicin;

(c) obtaining an insert DNA from a recombinant vector that forms part of the library and that has been screened as positive for the ability to convert carminomycin to daunorubicin; and (d) optionally, obtaining from the insert DNA a restriction fragment that contains a gene coding for carminomycin 4-O-methyltransferase.

The library may be prepared in step (a) by partially digesting the genomic DNA of *S. peucetius* 29050 or a strain derived therefrom. The restriction enzyme MboI is preferably used. The DNA fragments thus obtained can be size fractionated; fragments from 3 to 5 kb in size are preferred. These fragments are ligated into a linearized vector such as pWHM3 or plJ702. Host cells are transformed with the ligation mixture. Typically, the host cells can not produce carminomycin or daunorubicin and can be carminomycin- or daunorubicin-sensitive, for example, sensitive to 10 microgram or less of carminomycin or daunorubicin per ml. For example, *S. lividans* Jl1623 protoplasts (Hopwood et al., *Genetic manipulation of Streptomyces, A Laboratory Manual*, John Innes Foundation, Norwich, UK, 1985) may be transformed.

In step (b), the transformants thus contained are screened for the ability to take up carminomycin, convert it to daunorubicin, and excrete daunrorubicin. Clones able to convert carminomycin to daunorubicin are identified by chromatographic analysis of extracts of a culture medium containing carminomycin for the presence of daunorubicin. Such clones are isolated and recombinant vectors contained therein are extracted. On digestion of the recombinant vectors with suitable restriction enzymes in step (c), the *S. peucetius* 29050 DNA inserted into each vector may be identified, sized and mapped. In this way, it may be checked that the vector contains an insert DNA of the invention.

Further, two or more overlapping inserts may be isolated that are wholly or partly embraced within the DNA of the invention. These may be fused together by cleavage at a common restriction site and subsequent ligation to obtain a DNA of the invention, pared in length using appropriate restriction enzymes if necessary. Restriction fragments of an insert DNA that contains a gene coding for the COMT protein may be obtained in step (d) also by cleaving an insert DNA with an appropriate restriction enzyme.

DNA of the invention may be mutated in a way that does not affect its ability to confer the ability to convert carminomycin to daunorubicin. This can be achieved by site-directed mutagenesis for example. Such mutated DNA forms part of the invention.

The DNA of the invention may also be incorporated into vectors suitable for expression of the dnrK gene in a non-streptomycete host like *E. coli*.

The following examples illustrate the invention.

MATERIALS AND METHODS

Bacterial strains and plasmids: *E. coli* strain DH5α, which is sensitive to ampicillin and epramycin, is used for subcloning DNA fragments and *E. coli* K38 / Russel & Modet, *J. Bacteriol.* 159:1034 (1984) / is used for expression of the *S. Peucetius* dnrK gene, *E. coli* JM105 is used for making single stranded DNA for sequencing the DnK gene.

Media and buffers: *E. coli* DH5α is maintained on LB agar (Sambrook et al., *Molecular Cloning. A Laboratory Manual*, 2nd ed. Cold Spring Harbor Press, Cold Spring Harbor, N.Y., 1989). When selecting for transformants, ampicillin or epramycin are added at concentrations of 50 µg/ml and 100 µg/ml, respectively. *E. coli* JM105 is maintained on M9 minimal agar medium (Sambrook et al., *Molecular Cloning, A Laboratory Manual*, 2nd ed. Cold Spring Harbor Press, Cold Spring Harbor, N.Y., 1989), and a colony is transferred to LB medium and grown overnight at 37° C. to obtain the bacteria used in the preparation of single stranded DNA. H agar (Sambrook et al., *Molecular Cloning, A Laboratory Manual*, 2nd ed. Cold Spring Harbor Press, Cold Spring Harbor, N.Y., 1989) is used to plate *E. coli* DH5α transformed with the replicative form of M13 DNA [(Yansch-Perron et al., *Gene* 33:103 (1985)]. *S. lividans* is maintained on R2YE agar (Hopwood et al., *Genetic Manipulator, of Streptomyces, A Laboratory Manual*, John Innes Foundation, Norwich, UK, 1985) for the preparation of spores as well as for the regeneration of protoplasts.

Subcloning DNA fragments: DNA samples are digested with appropriate restriction enzymes and separated on agarose gels by standard methods (Saybrook et al., *Molecular Cloning, A Laboratory Manual*, 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.). The isolated DNA fragments are subcloned using standard techniques (Sambrook et al., *Molecular Cloning, A Laboratory Manual*, 2nd ed. Cold Spring Harbor Press, Cold Spring Harbor, N.Y. 1989) into *E. coli* and *E. coli*/Streptomyces shuttle vectors for biotransformation and expression experiments, respectively, and into M13 vectors [(Yansch-Perron et al., *Gene* 33:103 (1985)] for sequencing.

DNA sequencing: After subcloning DNA fragments of interest into an m13 vector, single stranded DNA is prepared by standard techniques (Sambrook et al., *Molecular Cloning, A Laboratory Manual*, 2nd ed. Cold Spring Harbor Press, Cold Spring Harbor, N.Y., 1989) and used in sequencing. DNA sequence data are obtained using a Sequenase version 2.0 sequencing kit (U.S. Biochemicals, Cleveland, Ohio) according to the manufacturers suggestions. 7-Deaza dGTP is used instead of dGTP to avoid compressions. Initially, an universal primer of the M13 vector is used to obtain the sequence of the first 200–250 bases, then from these sequence data, and 17-mer oligoncleotide is synthesised using an Applied Biosystems 391 DNA synthesizer according to the manufacturer's directions and used as a primer to continue DNA sequencing until the complete DNA sequence data are obtained.

Transformation of Streptomtces species and *E. coli*; Competent cells of *E. coli* are prepared by the calcium chloride method (Sambrook et al., *Molecular Cloning, A Laboratory Manual*, 2nd ed. Cold Spring Harbor Press, Cold Spring Harbor, N.Y., 1989) and transformed by standard techniques (Sambrook et al., *Molecular Cloning, A Laboratory Manual*, 2nd ed. Cold Spring Harbor Press, Cold Spring Harbor, N.Y., 1989). *S. lividans* TK24 mycelium is grown in YEME medium (Hopwood et al., *Genetic Manipulation of Streptomyces, A Laboratory Manual*, John Innes Foundation, Norwich, UK, 1985) and harvested after 48 hr. The mycelial pellet is washed twice with 10.3% sucrose solution and used to prepare protoplasts according to the method outlined in the Hopwood manual (Hopwood et al., *Genetic Manipulation of Streptomyces, A laboratory Manual*, John Innes Foundation, Norwich, UK, 1985). The protoplast pellet is suspended in about 300 microliters of P buffer (Hopwood et al., *Genetic Manipulation of Streptomyces. A Laboratory Manual*, John Innes Foundation, Norwich, UK, 1985) and a 50 microliter aliquot of this suspension is used for each transformation. Protoplasts are transformed with plasmid DNA according to the small-scale transformation method of Hopwood et al. (Hopwood et al., *Genetic Manipulation of Streptomyces, A Laboratory Manual*, John Innes Foundation, Norwich, UK, 1985). After 17 hr of regeneration of R2YE medium at 30° C., the plates are overlayed with 50 µg/ml of thiostrepton and allowed to grow at 30° C. until sporulated.

Bioconversion of carminomycin to daunorubicin: *S. lividans* transformants harboring different plasmids are inoculated into liquid R2YE medium (Hopwood et al., *Genetic Manipulation of Streptomyces. A Laboratory Manual*, John Innes Foundation, Norwich, UK, 1985) containing 5 µg/ml of thiostrepton. After 2 days of growth at 30° C., 2.5 ml of this culture is transferred to 25 ml of Strohl medium [(Dekleva et al., *Can J. Microbiol*, 31:287 (1985)] containing 20 µg/ml of thiostrepton. Cultures are grown in baffled Erlenmeyer flasks on a rotary shaker at 300 rpm at 30° C. for 72 hr, after which carminomycin (as a solution in water at a concentration of 10 milligrams/ml) is added to cultures to give a final concentration of 5 µg/ml. After 24 h of further incubation on the shaker, the cultures are incubated in a water bath at 60° C. for 45 min after the addition of 150 milligrams/ml of oxalic acid to hydrolize the glycosidic forms of the anthracycline metabolites. The metabolites are extracted from the cultures with 15 ml of chloroform after adjusting the pH of cultures to 8.4–8.6. The chloroform solution is filtered through a 0.45 µm Acrodisc CR filter (Gelman Sciences, Ann Arbor, Mich.) and 100 microliters of this filtrate is analyzed by HPLC on a Waters Nova-Pak $C_{15}$ cartridge (8 mm×10 cm) with a mobile phase of methanol-water (85:15) adjusted to pH 2.5 with phosphoric acid a; a flow rate of 3 ml/min. The column output was monitored using Waters 6000 solvent delivery system, a 441 UV detector operated at 254 nm, and a 740 data module. Carminomycin and daunorubicin (10 µg/ml in methanol) were used as external standards to quantitate the amount of these metabolites isolated from the cultures.

EXAMPLE 1

Cloning of the dnrK Gene Encoding Carminomycin 4-O-methyltransferase

Figure 2:
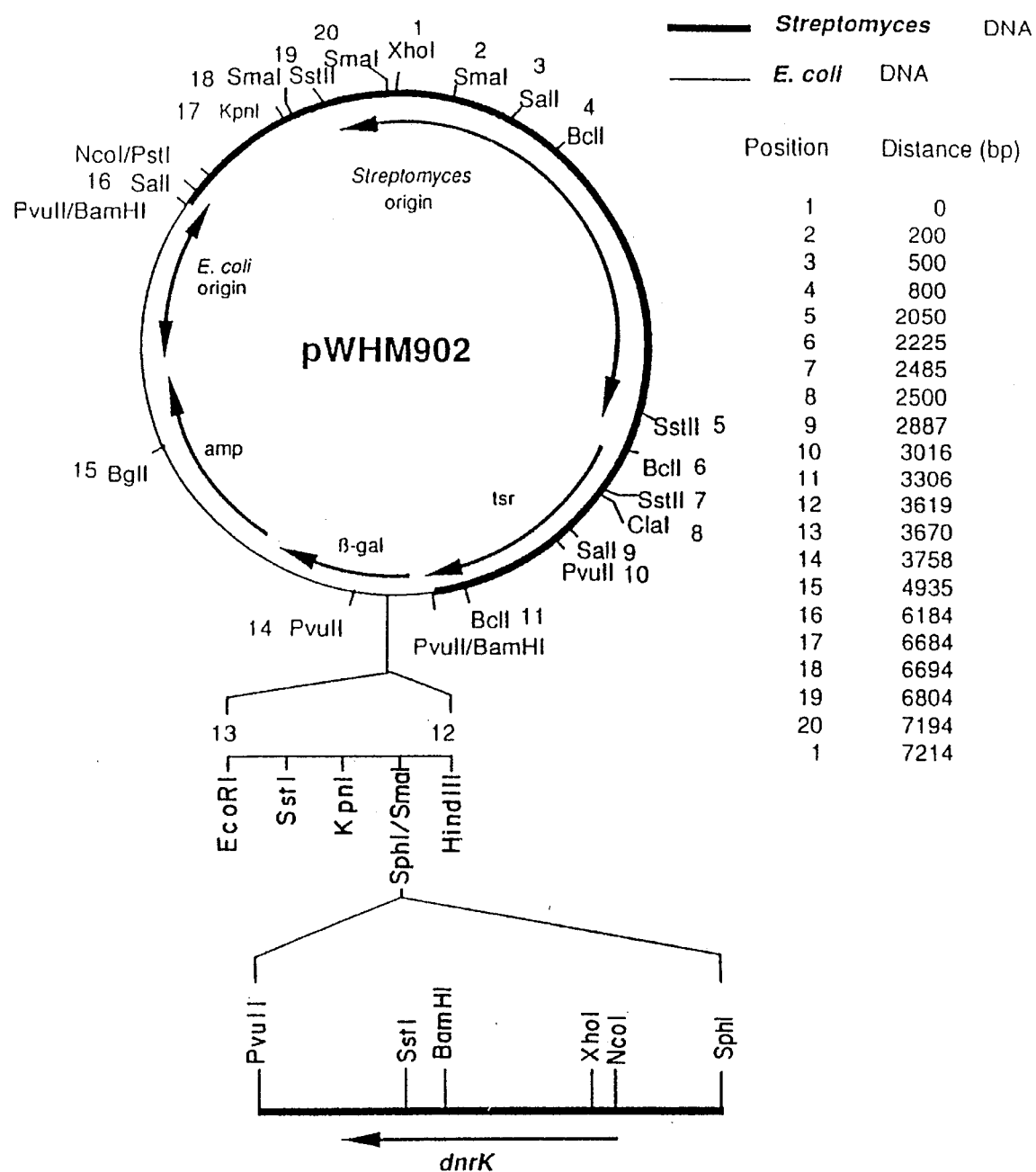
FIG. 2 is the restriction map analysis of the first DNA of the invention. This is an insert in recombinant plasmid pWHM902 that was constructed by insertion of a 1.6 kb SphI/PvuII DNA fragment containing the carminomycin 4-O-methyltransferase (dnrK) gene, which was obtained from recombinant plasmid pWHM901 by its digestion with SphI and PvuII, into the SphI/SmaI sites of the pWHM3 plasmid, an *Escherichia coli*-Streptomyces shuttle vector [Vara et al., *J Bacteriol.* 171:5872 (1989)]. The map shown in FIG. 2 does not necessarily provide an exhaustive listing of all restriction sites present in the DNA segment. However, the reported sites are sufficient for an unambiguous recognition of the segments.

Several of the cosmid clones described by Stutzman-Engwall and Hutchinson [(*Proc. Natl. Acad. Sci. USA* 86:3135 (1989)], representing approximately 96 kb of *S. peucetius* 29050 genomic DNA, are transformed into *S. lividans* TK24 and the transformants are analysed for the bioconversion of carminomycin to daunorubicin according to the method described in the materials and methods section. Cosmid clone pWHM339 [Otten et al., *J. Bacteriol.* 172:3427 (1990)] bioconverts 22% of added carminomycin to daunorubicin. A 11.2 kb EcoRl fragment from the insert in pWHM339 is subcloned into the cosmid vector pKC505 (Richardson et al., *Gene* 61:231 (1987)] to yield plasmid pWHM534. *S. lividans* TK24 transformed with pWHM534 shows a 25 to 60% bioconversion of added carminomycin to daunorubicin. A 5.8 kb Sphl fragment from pWHM534 is subcloned in the Sphl site of the high-copy number plasmid pWHM3 to yield the plasmid pWHM901. *S. lividans* transformed with pWHM901 exhibits a 50 to 85% bioconversion of carminomycin to daunorubicin. A 1.6 kb Sphl/Pvull fragment is cloned from pWHM901 first into the Sphl/Smal sites of pUC19 [Yansch-Perron et al., Gene 33:103 (1985)], then the 1.6 kb DNA fragment is subcloned from the latter plasmid as an HindIII/EcoRI fragment into the HindIII/EcoRI sites of pWHM3 to yield plasmid pWHM902 (FIG. 2). *S. lividans* transformed with pWHM902 bioconverts 100% of the carminomycin added to the culture to daunorubicin.

DNA Sequence of the Region Containing the dnrK Gene

Sequencing a 2.5 kb DNA segment of the 5.8 kb Sphl fragment in pWHM901 is carried out by subcloning 0.4 kb Spnl/Xhol, 0.7 kb Xhol/Sstl, 0.6-kb Sstl/Sall, and 0.8 kb Sall/Xhol fragments from pWHM902 into M13mp18 and -mp19 vectors [Yansch-Perron et al., *Gene* 33:103 (1985)] to obtain both orientations of each DNA segment. DNA sequencying of the resulting four clones is performed as described in the materials and methods section. The resulting DNA sequence of a 1.6 kb DNA fragment containing the dnrK gene, and the amino acid sequence of the COMT protein deduced by analysis of this DNA sequence with the CODON PREFERENCE program described by Devereux et al. [*Nucl Acics Res.* 12:387 (1984)], are shown in FIG. 3. The dnrK open reading frame identified by CODONPREFERENCE and TRANSLATE analysis [Devereux et al., *Nucl. Acids Res.* 12:387 (1984)] codes for the COMT protein.

EXAMPLE 2

Construction of a Vector for Expression of the dnrK Gene in *E. coli*

An approx. 1.6 kb Sphl/Pvull DA fragment containing the entire dnrK open reading frame along with some flanking sequence (FIG. 3) is subcloned into Sph/l and Smal-digested pUC19 [Yansch-Perron et al., *Gene* 33:103 (1985) to give the plasmid pWHM904 (not shown). The following two oligodeoxynucleotide primers, corresponding to sequences on either side of the dnrK-containing fragment to be amplified, are synthesized with an Applied Biosystems 391 DA synthesizer according to the manufacturer's directions:

---

XbaI   BamHI   rbs           NdeI
5' - GGG TCTAGA GGATCC AGGAG CAG CATATG ACC GCT GAA CCG ACC GTC GCG GCC
     CGG CCG CAG CAG AT - 3': Primer #1 (SEQ ID NO:3)
                                                        SphI    PstI
3' - AC CGC TAG CCT GAC GAG CTC CTC CGTACG GACGTC CCC - 5': Primer #2 (SEQ ID NO:4)

---

The third position of second, third and sixth codons (indicated by bold face letters) of the dnrK gene is changed by using primer #1 to reflect the most frequently used codon in highly expressed *E. coli* genes as a menas to enhance the expression of the dnrK gene in *E. coli*:

---

ATG ACC GCT GAA CCG ACC GTC GCG GCC CGG CCG CAG CAGA: Mutated sequence (SEQ ID NO:5)
ATG ACA GCC GAA CCG ACG GTC GCG GCC CGG CCG CAG CAGA: Wild type sequence (SEQ ID NO:6)

---

Figure 4:
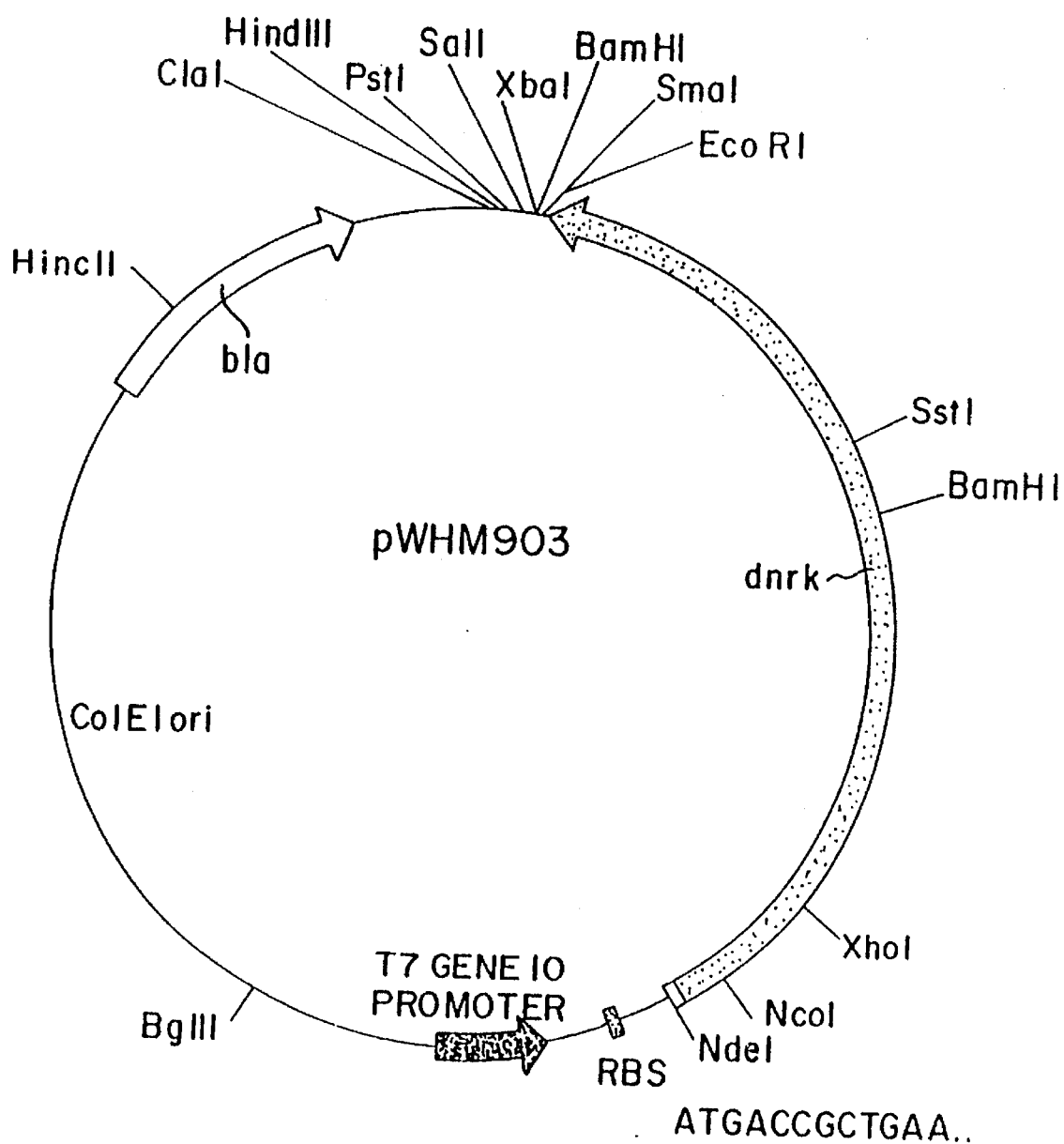
FIG. 4 is the restriction map analysis of the second DNA of the invention. This is an insert in recombinant plasmid pWHM903 that was constructed by insertion of a ≈1.4 kb NdeI/EcoRl DNA fragment, obtained from the 5.8 kb SphI DNA fragment of pWHM901 by site-directed mutagenesis, into the NdeI and EcoRl sites of the pT7—7 E. coli expression plasmid vector [Tabor and Richardson, *Proc Natl. Acad. Sci. USA* 82:1074 (1985)]. The map shown in FIG. 4 does not necessarily provide an exhaustive listing of all restriction sites present in the DNA segment. However, the reported sites are sufficient for an unambiguous recognition of the segments.

These two primers are used to amplify the dnrK sequence of pWHM904 from nucleotides 205 (the beginning of the dnrK orf) to 445 of FIG. 3 by standard methods for the polymerase chain reaction with Streptomyces DNA [for example, see Guilfoile and Hutchinson, *J. Bacteriol.* 174:3659 (1992)]. From the amplified product, an 88 bp NdeI/NcoI fragment is excised and ligated to a 1.3 kb NcoI/EcoRl fragment (obtained from pWHM902), containing the remaining dnrK gene (FIGS. 2 and 3), and Ndel/EccRl-digested pT7—7 [Tabor and Richardson, *Proc. atl. Acad. Sci. A* 82:1074 (1985)], which results in the fusion of the dnrK orf to the T7 gene 10 promoter of this *E. coli* expression vector. Competent cells of *E. coli* DH5α are transformed with the ligated DNA and transformants were screened for pT7—7 with dnrK. The resulting plasmid is designated pWHM903 (FIG. 4). cl Expression of the DnrK Gene in *E. coli*

Competent *E. coli* cells containing the plasmid pGP1-2 [Tabor and Richardson] were selected on LB agar (Sambrook et al., *Molecular Cloning, A Laboratory Manual*, 2nd ed. Cold Spring Harbor Press, Cold Spring Harbor, N.Y., 1989) containing ampicillin (100 µg/ml) and kanamycin (50 µg/ml) after growth at 30° C. The procedure for preparing competent cells of *E. coli* containing pGP1-2 is the same as that for any other *E. coli* strain, except that the cultures are maintained at 30° C. instead of 37° C. Competent cells of *E. coli* containing pGP1-2 are prepared from cells grown at 30° C. to a $OD_{550}$ of 0.5 to 0.6 in LB medium containing kanamycin. It is very important to maintain strains containing pGP1-2 at 30° C. for routine maintenance and pre-induction growth to avoid over expression of T7 RNA polymerase which might otherwise result in a mutated plasmid.

A single transformant harboring both pGP1-2 and pWHM903 is inoculated into 25 ml of 2×YT medium (Sambrook et al., *Molecular Cloning, A Laboratory Manual*, 2nd ed. Cold Spring Harbor Press, Cold Spring Harbor, N.Y., 1989) containing 100 µg/ml ampicillin and 50 µg/ml kanamycin and grown overnight at 30° C. with vigorous agitation. The next morning cultures are heat shocked at 42° C. for 30 min in a shaking water bath and then transferred back to 30° C. After 90 min further incubation, one ml of the culture is centrifuged at 14,000 rpm in a microcentrifuge for 1 min, the supernatant is discarded, and the cell pellet is resuspended in 100 microliters of Laemmli buffer [Laemmli, Nature (London), 227:680 (1970)] and boiled for 5 min. The proteins contained in the boiled sample are analyzed on a 10% SDS-polyacrylamide gel using standard methods [Laemmli, *Nature* (London), 227:680 (1970)] by comparison with the proteins obtained from the cell extract of *E. coli* transformed with the pt7—7 vector that does not contain the dnrK gene. The COMT protein migrates at $M_r$ 38,700.

EXAMPLE 3

Conversion of Carminomycin to Daunorubicin by a Cell Containing the COMT Protein A single *E. coli* transformant harboring both pGP1-2 and pWHM903 was inoculated into 25 ml of 2×YT medium containing 100 µg/ml ampicillin and 50 µg/ml kanamycin and grown overnight at 30° C. with vigorous agitation. The next morning cultures are heat shocked at 42° C. for 30 min in a shaking water bath and then transferred back to 30° C. after adding 5 µg/ml of carminomycin. The cultures are allowed to grow for additional 90 min, after which the anthracycline metabolites are isolated using standard methods and analysed on HPLC. Comparison of the relative areas of the signal peaks for carminomycin and daunorubicin in the HPLC chromatogram indicates that 75 to 80% of the carminomycin added to the culture medium is converted to daunorubicin.

We claim:

1. An isolated and purified DNA sequence consisting of a gene which codes for carminomycin 4-O-methyltransferase, wherein said gene has the sequence shown in SEQ ID NO: 1.

2. A heterologous vector comprising a DNA sequence according to claim 1.

3. The vector according to claim 2, wherein said vector is a plasmid.

4. The vector according to claim 3, wherein said plasmid is selected from the group consisting of pWHM901, pWHM902 and pWHM903.

5. A host cell transformed with a vector according to claim 2.

6. The host cell according to claim 5, wherein said vector is a plasmid.

7. The host cell according to claim 6, wherein said host cell is selected from the group consisting of E. coli and Streptomyces.

8. The host cell according to claim 6, wherein said plasmid is selected from the group consisting of pWH901, pWHM902 and pWH903.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1632 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 204..1271

( x i ) SEQUENCE DESCRIPTION: SEQ ID NO:1:

```
GCATGCCGGC  AACCGGGCGC  CGGTTCTCCG  GTGAGCAGAT  CCACCTCATC  CGCATCGTCG        60

ACGGCAAGAT  CCGCGATCAC  CGCGACTGGC  CCGACTACCT  CGGCACCTAC  CGCCAGCTCG       120

GCGAGCCCTG  GCCCACCCCC  GAGGGCTGGC  GCCCCTGACC  CCCCATCACC  CCGCCGACGC       180

CACGACAGGA  GCACGGACAC  ACC  ATG  ACA  GCC  GAA  CCG  ACG  GTC  GCG  GCC    230
                             Met  Thr  Ala  Glu  Pro  Thr  Val  Ala  Ala
                              1                 5
```

-continued

| | | | | | | | | | | | | | | | | |
|---|---|---|---|---|---|---|---|---|---|---|---|---|---|---|---|---|
| CGG | CCG | CAG | CAG | ATC | GAC | GCC | CTC | AGG | ACC | CTG | ATC | CGC | CTC | GGA | AGC | 278 |
| Arg | Pro | Gln | Gln | Ile | Asp | Ala | Leu | Arg | Thr | Leu | Ile | Arg | Leu | Gly | Ser | |
| 10 | | | | 15 | | | | | 20 | | | | | | 25 | |
| CTG | CAC | ACG | CCC | ATG | GTC | GTC | CGG | ACG | GCC | GCC | ACC | CTG | CGG | CTC | GTC | 326 |
| Leu | His | Thr | Pro | Met | Val | Val | Arg | Thr | Ala | Ala | Thr | Leu | Arg | Leu | Val | |
| | | | | 30 | | | | | 35 | | | | | 40 | | |
| GAC | CAC | ATC | CTG | GCC | GGG | GCC | CGC | ACC | GTG | AAG | GCC | CTG | GCG | GCC | AGG | 374 |
| Asp | His | Ile | Leu | Ala | Gly | Ala | Arg | Thr | Val | Lys | Ala | Leu | Ala | Ala | Arg | |
| | | | 45 | | | | | 50 | | | | | 55 | | | |
| ACA | GAC | ACC | CGG | CCG | GAA | GCA | CTC | CTG | CGA | CTG | ATC | CGC | CAC | CTG | GTG | 422 |
| Thr | Asp | Thr | Arg | Pro | Glu | Ala | Leu | Leu | Arg | Leu | Ile | Arg | His | Leu | Val | |
| | | 60 | | | | | 65 | | | | | 70 | | | | |
| GCG | ATC | GGA | CTG | CTC | GAG | GAG | GAC | GCA | CCG | GGC | GAG | TTC | GTC | CCG | ACC | 470 |
| Ala | Ile | Gly | Leu | Leu | Glu | Glu | Asp | Ala | Pro | Gly | Glu | Phe | Val | Pro | Thr | |
| | 75 | | | | | 80 | | | | | 85 | | | | | |
| GAG | GTC | GGC | GAG | CTG | CTC | GCC | GAC | GAC | CAC | CCA | GCC | GCG | CAG | CGT | GCC | 518 |
| Glu | Val | Gly | Glu | Leu | Leu | Ala | Asp | Asp | His | Pro | Ala | Ala | Gln | Arg | Ala | |
| 90 | | | | | 95 | | | | | 100 | | | | | 105 | |
| TGG | CAC | GAC | CTG | ACG | CAG | GCC | GTG | GCG | CGC | GCC | GAC | ATC | TCC | TTC | ACC | 566 |
| Trp | His | Asp | Leu | Thr | Gln | Ala | Val | Ala | Arg | Ala | Asp | Ile | Ser | Phe | Thr | |
| | | | | 110 | | | | | 115 | | | | | 120 | | |
| CGC | CTC | CCC | GAC | GCC | ATC | CGT | ACC | GGC | CGC | CCC | ACG | TAC | GAG | TCC | ATC | 614 |
| Arg | Leu | Pro | Asp | Ala | Ile | Arg | Thr | Gly | Arg | Pro | Thr | Tyr | Glu | Ser | Ile | |
| | | | 125 | | | | | 130 | | | | | 135 | | | |
| TAC | GGC | AAG | CCG | TTC | TAC | GAG | GAC | CTG | GCC | GGC | CGC | CCC | GAC | CTG | CGC | 662 |
| Tyr | Gly | Lys | Pro | Phe | Tyr | Glu | Asp | Leu | Ala | Gly | Arg | Pro | Asp | Leu | Arg | |
| | | 140 | | | | | 145 | | | | | 150 | | | | |
| GCG | TCC | TTC | GAC | TCG | CTG | CTC | GCC | TGC | GAC | CAG | GAC | GTC | GCC | TTC | GAC | 710 |
| Ala | Ser | Phe | Asp | Ser | Leu | Leu | Ala | Cys | Asp | Gln | Asp | Val | Ala | Phe | Asp | |
| | 155 | | | | | 160 | | | | | 165 | | | | | |
| GCT | CCG | GCC | GCC | GCG | TAC | GAC | TGG | ACG | AAC | GTC | CGG | CAT | GTG | CTC | GAC | 758 |
| Ala | Pro | Ala | Ala | Ala | Tyr | Asp | Trp | Thr | Asn | Val | Arg | His | Val | Leu | Asp | |
| 170 | | | | | 175 | | | | | 180 | | | | | 185 | |
| GTG | GGT | GGC | GGC | AAG | GGT | GGT | TTC | GCC | GCG | GCC | ATC | GCG | CGC | CGG | GCC | 806 |
| Val | Gly | Gly | Gly | Lys | Gly | Gly | Phe | Ala | Ala | Ala | Ile | Ala | Arg | Arg | Ala | |
| | | | | 190 | | | | | 195 | | | | | 200 | | |
| CCG | CAC | GTG | TCG | GCC | ACC | GTG | CTG | GAG | ATG | GCG | GGC | ACC | GTG | GAC | ACC | 854 |
| Pro | His | Val | Ser | Ala | Thr | Val | Leu | Glu | Met | Ala | Gly | Thr | Val | Asp | Thr | |
| | | | 205 | | | | | 210 | | | | | 215 | | | |
| GCC | CGC | TCC | TAC | CTG | AAG | GAC | GAG | GGC | CTC | TCC | GAC | CGT | GTC | GAC | GTC | 902 |
| Ala | Arg | Ser | Tyr | Leu | Lys | Asp | Glu | Gly | Leu | Ser | Asp | Arg | Val | Asp | Val | |
| | | 220 | | | | | 225 | | | | | 230 | | | | |
| GTC | GAG | GGG | GAC | TTC | TTC | GAG | CCG | CTG | CCC | CGC | AAG | GCG | GAC | GCG | ATC | 950 |
| Val | Glu | Gly | Asp | Phe | Phe | Glu | Pro | Leu | Pro | Arg | Lys | Ala | Asp | Ala | Ile | |
| | 235 | | | | | 240 | | | | | 245 | | | | | |
| ATC | CTC | TCT | TTC | GTC | CTC | CTC | AAC | TGG | CCG | GAC | CAC | GAC | GCC | GTC | CGG | 998 |
| Ile | Leu | Ser | Phe | Val | Leu | Leu | Asn | Trp | Pro | Asp | His | Asp | Ala | Val | Arg | |
| 250 | | | | | 255 | | | | | 260 | | | | | 265 | |
| ATC | CTC | ACC | CGC | TGC | GCC | GAG | GCC | CTG | GAG | CCC | GGC | GGG | CGC | ATC | CTG | 1046 |
| Ile | Leu | Thr | Arg | Cys | Ala | Glu | Ala | Leu | Glu | Pro | Gly | Gly | Arg | Ile | Leu | |
| | | | | 270 | | | | | 275 | | | | | 280 | | |
| ATC | CAC | GAG | CGC | GAC | GAC | CTC | CAC | GAG | AAC | TCG | TTC | AAC | GAA | CAG | TTC | 1094 |
| Ile | His | Glu | Arg | Asp | Asp | Leu | His | Glu | Asn | Ser | Phe | Asn | Glu | Gln | Phe | |
| | | | 285 | | | | | 290 | | | | | 295 | | | |
| ACA | GAG | CTC | GAT | CTG | CGG | ATG | CTG | GTC | TTC | CTC | GGC | GGT | GCC | CTG | CGC | 1142 |
| Thr | Glu | Leu | Asp | Leu | Arg | Met | Leu | Val | Phe | Leu | Gly | Gly | Ala | Leu | Arg | |
| | | 300 | | | | | 305 | | | | | 310 | | | | |
| ACC | CGC | GAG | AAG | TGG | GAC | GGC | CTG | GCC | GCG | TCG | GCG | GGC | CTC | GTG | GTC | 1190 |
| Thr | Arg | Glu | Lys | Trp | Asp | Gly | Leu | Ala | Ala | Ser | Ala | Gly | Leu | Val | Val | |
| | 315 | | | | | 320 | | | | | 325 | | | | | |

| | | | | | | | | | | | | | | | | |
|---|---|---|---|---|---|---|---|---|---|---|---|---|---|---|---|---|
| GAG | GAG | GTG | CGG | CAA | CTG | CCG | TCG | CCG | ACC | ATC | CCG | TAC | GAC | CTC | TCG | 1238 |
| Glu | Glu | Val | Arg | Gln | Leu | Pro | Ser | Pro | Thr | Ile | Pro | Tyr | Asp | Leu | Ser | |
| 330 | | | | | 335 | | | | 340 | | | | | | 345 | |
| CTC | CTC | GTC | CTT | GCC | CCC | GCG | GCC | ACC | GGC | GCC | TGACACACGA | | GGTACGGGAA | | | 1291 |
| Leu | Leu | Val | Leu | Ala | Pro | Ala | Ala | Thr | Gly | Ala | | | | | | |
| | | | | 350 | | | | | 355 | | | | | | | |

| | | | | |
|---|---|---|---|---|
| GGGTTCATCA | GCAATGCCGA | CACGCATGAT | CACCAACGAT | GAGGTGACCC | TGTGGAGCGA | 1351 |
| AGGGCTCGGC | GATCCGGCCG | ACGCCCCGTT | GCTCCTGATC | GCCGGCGGCA | ACCTCTCGGC | 1411 |
| CAAATCGTGG | CCGGACGAGT | TCGTCGAACG | CCTGGTCGCG | GCCGGGCACT | TCGTGATCCG | 1471 |
| CTACGACCAC | CGGGACACCG | GGCGCTCCTC | CCGGTGCGAC | TTCGCGCTCC | ACCCCTACGG | 1531 |
| CTTCGACGAG | CTGGCCGCCG | ACGCGCTGGC | CGTCCTGGAC | GGCTGGCAGG | TCCGCGCCGC | 1591 |
| CCATGTGGTG | GGCATGTCGC | TGGGCAACAC | CATCGGCCAG | C | | 1632 |

( 2 ) INFORMATION FOR SEQ ID NO:2:

( i ) SEQUENCE CHARACTERISTICS:
        ( A ) LENGTH: 356 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Ala Glu Pro Thr Val Ala Ala Arg Pro Gln Gln Ile Asp Ala
 1               5                  10                  15

Leu Arg Thr Leu Ile Arg Leu Gly Ser Leu His Thr Pro Met Val Val
            20                  25                  30

Arg Thr Ala Ala Thr Leu Arg Leu Val Asp His Ile Leu Ala Gly Ala
            35                  40                  45

Arg Thr Val Lys Ala Leu Ala Ala Arg Thr Asp Thr Arg Pro Glu Ala
        50                  55                  60

Leu Leu Arg Leu Ile Arg His Leu Val Ala Ile Gly Leu Leu Glu Glu
65                  70                  75                  80

Asp Ala Pro Gly Glu Phe Val Pro Thr Glu Val Gly Glu Leu Leu Ala
                85                  90                  95

Asp Asp His Pro Ala Ala Gln Arg Ala Trp His Asp Leu Thr Gln Ala
            100                 105                 110

Val Ala Arg Ala Asp Ile Ser Phe Thr Arg Leu Pro Asp Ala Ile Arg
            115                 120                 125

Thr Gly Arg Pro Thr Tyr Glu Ser Ile Tyr Gly Lys Pro Phe Tyr Glu
        130                 135                 140

Asp Leu Ala Gly Arg Pro Asp Leu Arg Ala Ser Phe Asp Ser Leu Leu
145                 150                 155                 160

Ala Cys Asp Gln Asp Val Ala Phe Asp Ala Pro Ala Ala Ala Tyr Asp
                165                 170                 175

Trp Thr Asn Val Arg His Val Leu Asp Val Gly Gly Gly Lys Gly Gly
            180                 185                 190

Phe Ala Ala Ala Ile Ala Arg Arg Ala Pro His Val Ser Ala Thr Val
            195                 200                 205

Leu Glu Met Ala Gly Thr Val Asp Thr Ala Arg Ser Tyr Leu Lys Asp
        210                 215                 220

Glu Gly Leu Ser Asp Arg Val Asp Val Val Glu Gly Asp Phe Phe Glu
225                 230                 235                 240

Pro Leu Pro Arg Lys Ala Asp Ala Ile Ile Leu Ser Phe Val Leu Leu
                245                 250                 255
```

| Asn | Trp | Pro | Asp | His | Asp | Ala | Val | Arg | Ile | Leu | Thr | Arg | Cys | Ala | Glu |
|---|---|---|---|---|---|---|---|---|---|---|---|---|---|---|---|
| | | | 260 | | | | | 265 | | | | | 270 | | |

| Ala | Leu | Glu | Pro | Gly | Gly | Arg | Ile | Leu | Ile | His | Glu | Arg | Asp | Asp | Leu |
|---|---|---|---|---|---|---|---|---|---|---|---|---|---|---|---|
| | | | 275 | | | | | 280 | | | | | 285 | | |

| His | Glu | Asn | Ser | Phe | Asn | Glu | Gln | Phe | Thr | Glu | Leu | Asp | Leu | Arg | Met |
|---|---|---|---|---|---|---|---|---|---|---|---|---|---|---|---|
| | 290 | | | | | 295 | | | | | 300 | | | | |

| Leu | Val | Phe | Leu | Gly | Gly | Ala | Leu | Arg | Thr | Arg | Glu | Lys | Trp | Asp | Gly |
|---|---|---|---|---|---|---|---|---|---|---|---|---|---|---|---|
| 305 | | | | | 310 | | | | | 315 | | | | | 320 |

| Leu | Ala | Ala | Ser | Ala | Gly | Leu | Val | Val | Glu | Glu | Val | Arg | Gln | Leu | Pro |
|---|---|---|---|---|---|---|---|---|---|---|---|---|---|---|---|
| | | | | 325 | | | | | 330 | | | | | 335 | |

| Ser | Pro | Thr | Ile | Pro | Tyr | Asp | Leu | Ser | Leu | Leu | Val | Leu | Ala | Pro | Ala |
|---|---|---|---|---|---|---|---|---|---|---|---|---|---|---|---|
| | | | 340 | | | | | 345 | | | | | 350 | | |

| Ala | Thr | Gly | Ala |
|---|---|---|---|
| | | 355 | |

( 2 ) INFORMATION FOR SEQ ID NO:3:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

```
GGGTCTAGAG GATCCAGGAG CAGCATATGA CCGCTGAACC GACCGTCGCG GCCCGGCCGC        60

AGCAGAT                                                                  67
```

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

```
ACCGCTAGCC TGACGAGCTC CTCCGTACGG ACGTCCCC                                38
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
ATGACCGCTG AACCGACCGT CGCGGCCCGG CCGCAGCAGA                              40
```

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

ATGACAGCCG AACCGACGGT CGCGGCCCGG CCGCAGCAGA                40